US009003893B2

(12) United States Patent
Tilley

(10) Patent No.: US 9,003,893 B2
(45) Date of Patent: Apr. 14, 2015

(54) CHAIN LINK TESTER

(71) Applicant: R.J. Reynolds Tobacco Company, Winston-Salem, NC (US)

(72) Inventor: Timothy Tilley, Pinnacle, NC (US)

(73) Assignee: R.J. Reynolds Tobacco Company, Winston-Salem, NC (US)

( * ) Notice: Subject to any disclaimer, the term of this patent is extended or adjusted under 35 U.S.C. 154(b) by 59 days.

(21) Appl. No.: 13/788,795

(22) Filed: Mar. 7, 2013

(65) Prior Publication Data
US 2014/0251024 A1 Sep. 11, 2014

(51) Int. Cl.
*G01N 3/22* (2006.01)
*B25B 13/00* (2006.01)

(52) U.S. Cl.
CPC ........................................ *G01N 3/22* (2013.01)

(58) Field of Classification Search
CPC .................................................... G01M 13/023
USPC .......................... 73/847, 828; 81/180.1, 185.2
See application file for complete search history.

(56) References Cited

U.S. PATENT DOCUMENTS

| 3,972,221 | A | 8/1976 | Natens et al. |
| 5,501,107 | A | 3/1996 | Snyder et al. |
| 6,361,111 | B1 | 3/2002 | Bowers et al. |
| 7,174,817 | B1 | 2/2007 | Hsieh |
| 7,237,376 | B1 | 7/2007 | Shirley et al. |
| 2011/0271969 | A1 | 11/2011 | Bullins et al. |

FOREIGN PATENT DOCUMENTS

| JP | 2004020453 | 1/2004 |
| WO | 2012026826 | 3/2012 |

OTHER PUBLICATIONS

Author: unknown, Title: Torque Manual, Date: Dec. 20, 2009, Publisher: Hand Tool Division of Dresser Industries, Inc., pp. 1-46.*
Author: unknown, Title: Adjustable Pry Bar IPA787, Date: May 5, 2009, Publisher: etoolcart.com, Automotive Specialty Tools, Inc., pp. 1.*
All-Spec Industries; Products for Electronic Service, Repair and Testing; www.all-spec.com/products/tools%7Cwrenches_and_sockets%7CTOL-47/?gclid=CNzlitrK-LqCFQ0GnQodl2QAMQ; Jan. 22, 2013; pp. 1-9.

* cited by examiner

*Primary Examiner* — Harshad R Patel
(74) *Attorney, Agent, or Firm* — Middleton Reutlinger; John Salazar

(57) ABSTRACT

A chain link tester and method of use is disclosed herein. The chain link tester may contain a tapered lever and may be adapted to operatively connect to a torque metering device. The chain link tester may be used to test chain links.

16 Claims, 5 Drawing Sheets

CHAIN LINK TESTER

FIELD OF THE INVENTION

The present invention is related generally to tools for testing equipment, and more specifically to a chain link testing device for chain links.

BACKGROUND OF THE INVENTION

It is often desirable to drive a conveyor belt using a chain-and-sprocket mechanism or drive. A chain-and-sprocket drive may be used in any of a variety of applications. Some examples of applications that may employ a chain-and-sprocket drive relate to converting materials from small fibers or pieces into a sheet, mat, or web for processing. One way to do this is to mix the fibers or pieces with water or other liquid into a slurry and then pour the slurry onto a surface so that it may settle into the desired form, which may be a sheet, mat, or web (hereinafter "web"). The extra water or other liquid (hereinafter "liquid") may then be allowed to dry off, leaving the small fibers or pieces congealed together in the desired web form. In order to decrease the drying time required, and thus improve the efficiency of the process, a dryer may be used. For example, the dryer may be an oven that subjects the slurry to an elevated temperature, thus increasing the evaporation rate of the liquid and decreasing the dry time. For large scale processes, the slurry may be conveyed through the dryer oven at a speed and temperature to evaporate a desirable amount of liquid from the web.

In some applications using a chain-and-sprocket mechanism to drive a conveyor belt, the chain may be heated when passing through a dryer oven, and then cooled when out of the oven. Repeated heating and cooling of the chain subjects the chain to thermal stresses that challenge the integrity of the chain and thus may shorten the chain's service life. Chain failure may be especially problematic in large scale operations or operations that are continuous for long periods of time. Down time may be extremely costly to the operator, as production is consequently slowed or stopped. In some applications, a chain may have hundreds or thousands of links and thus be extremely expensive to purchase or replace. Thus, it is desirable to test individual chain links for fatigue or other signs of wear so that, if such signs are found, appropriate remedial action may be taken to, for example, avoid expensive downtime and/or chain replacement.

Thus, there is a need in the art for a tool that can be quickly and efficiently used to consistently test chain links for signs of fatigue.

SUMMARY OF THE INVENTION

The presently described embodiments allow an operator to readily test and/or inspect the integrity of individual chain links of a chain, and thereby test and/or inspect the integrity of the overall chain. However, chains in use in some applications, such as, for example, those in use in industrial conveyor belts, may be very long. It may be difficult to consistently and efficiently test a large number of chain links due to, for example, operator fatigue. Thus, various embodiments described herein facilitate testing and/or inspection of the individual chain links by providing a chain link tester that is adapted for use with a torque metering device, such as, for example, a device one might find in a torque wrench or a torque ratchet, that can indicate to an operator when a predetermined amount of torque has been applied to each chain link. In this way, a consistent amount of torque may be applied to each chain link.

Therefore, various embodiments provide a chain link tester for consistently testing chain links.

Additional embodiments described herein provide a chain link tester that is dimensioned to fit and/or wedge between the chain links and the mechanism driving the chain, such as, for example, a sprocket. In some applications, it may be desirable to use a chain and/or a sprocket dimensioned within close tolerances. Thus, it may be desirable to dimension the chain link tester to correspond to the chain and/or sprocket and thereby enhance the consistency and/or the effectiveness of the chain link tester.

Various alternative structures and applications will become apparent from the following description taken in connection with the accompanying drawings, wherein some embodiments are set forth by way of illustration and examples.

DETAILED DESCRIPTION

Figure 1:
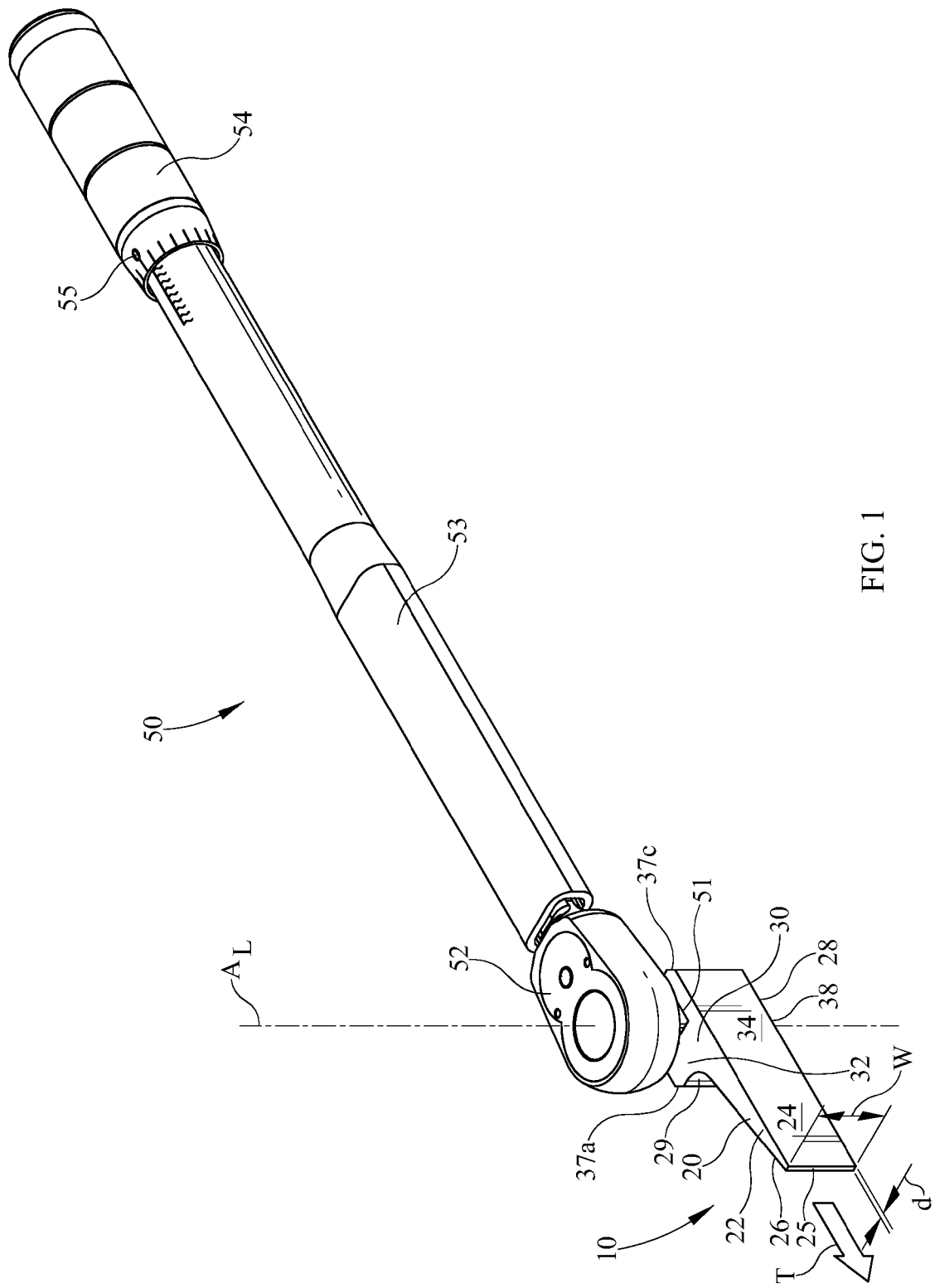
FIG. 1 is a perspective view of an embodiment of a chain link testing device.

It is to be understood that the various embodiments described herein are not limited in their application to the details of construction and the arrangement of components set forth in the following description or illustrated in the drawings. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," "in communication with" and "mounted," and variations thereof herein are used broadly and encompass direct and indirect connections, couplings, and mountings. In addition, the terms "connected" and "coupled" and variations thereof are not restricted to physical or mechanical connections or couplings.

Furthermore, and as described in subsequent paragraphs, the specific mechanical configurations illustrated in the drawings are intended to exemplify embodiments and other alternative mechanical configurations are possible.

Figure 2:
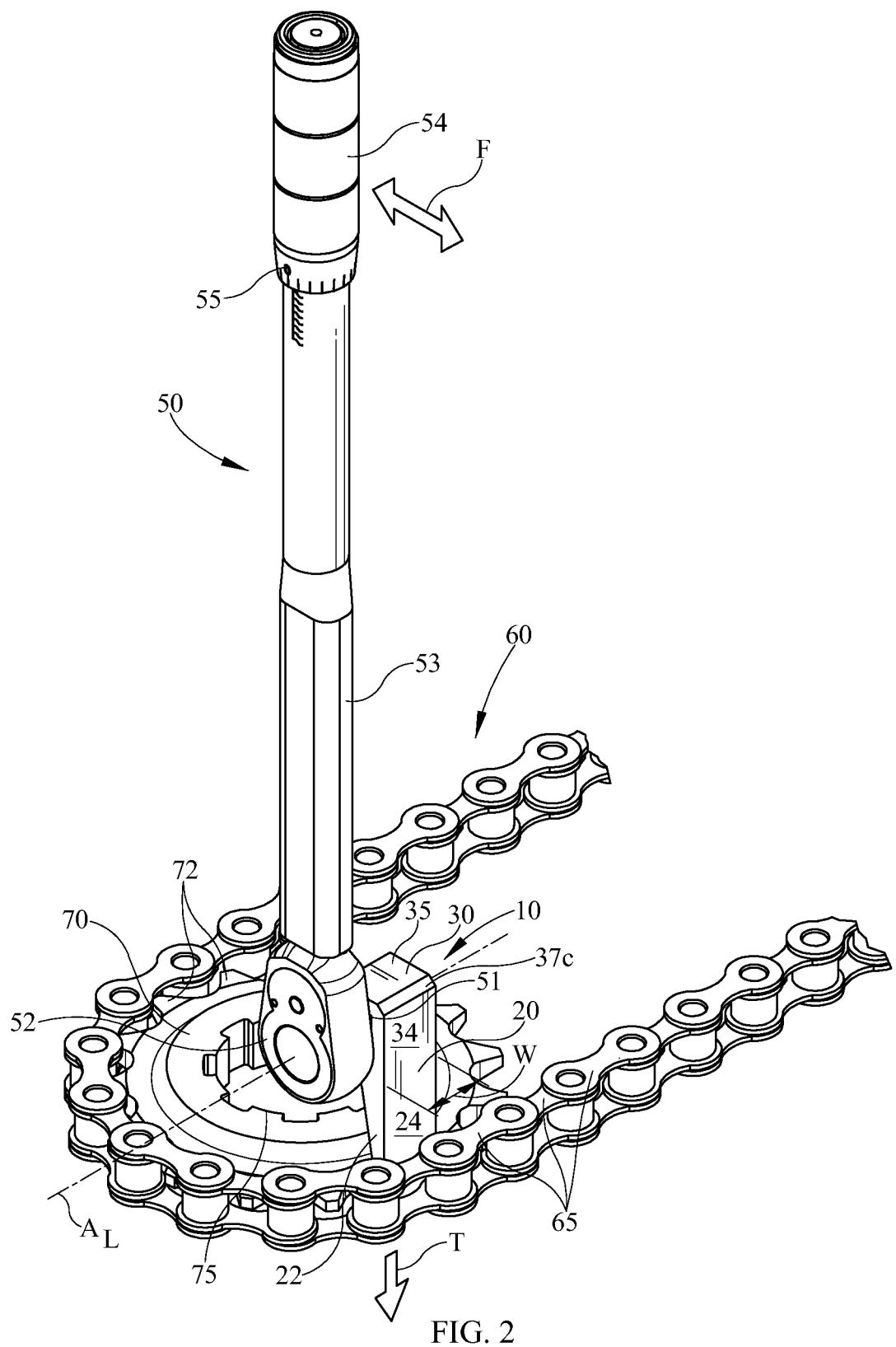
FIG. 2 is a perspective view of the chain link testing device of FIG. 1 engaging a chain and sprocket.

Referring to FIGS. 1 and 2, an embodiment of a chain link tester 10 is illustrated operatively connected to a torque metering device, or torque wrench or torque ratchet, 50. Chain link tester 10 has a base 30 that is connected to a head 52 of torque wrench 50. Chain link tester 10 has tapered lever 20 coupled to base 30 and extending outwardly from base 30 to lever end 25. In FIG. 2, a portion of tapered lever 20 is inserted between a chain 60 and a sprocket 70. In this way, a force may be applied in a force direction F to torque wrench 50 and transferred to a chain link 65 via a portion of chain link tester 10, wherein force F creates a reactionary torque or force at the chain link 65. This reactionary torque or force may be used to test the integrity and/or strength of the chain link 65 by, for example, causing the chain link to crack or split or otherwise show a sign of failure, or causing any existing cracks or splits or other sign of failure to become exaggerated.

Any of a variety of torque metering devices may be used in connection with chain link tester 10. It is understood that the Figures merely illustrate one embodiment of a torque metering device. It may be desirable, however, to provide a torque metering device, such as torque wrench 50, having a handle 54, a dial 55, a body 53, a head (of said torque metering device) 52, and engaging extension 51. Some such torque wrenches or ratchets may be commercially available, for example, from any of a variety of tool retailers or home improvement stores. In the embodiments illustrated, head 52 includes a torque limiting device for limiting the amount of torque that may be transmitted through it from body 53 and/or handle 54 to engaging extension 51 and to chain link tester 10. Head 52 also includes an indicator, or torque metering device, to alert the operator when a pre-determined amount of torque is applied to head 52. The indication made by the indicator may be any of a variety of indications, including, but not limited to, audible, such as, for example, a click, pop, buzz, or other noise; it may be visible, such as a light, a gauge, or metering device; the indication may be directed at a sense other than hearing or sight, such as, for example, feel, wherein the indication may be, for example, slip or vibration; the indication may be an electronic, digital, radio, or any other type of signal, which in turn may be transmitted or communicated to another device; or the indication may be any combination thereof. Dial 55 may be used to set the pre-determined torque. Handle 54 may provide a convenient and/or comfortable grip for a human operator, who may apply a force at handle 54 in force direction F. It is understood that a force may be applied at or near handle 54 or virtually anywhere on torque wrench 50, although it may be desirable to apply the force at handle 54 to optimize the reactionary force on the chain link 65 and/or sprocket 70. It is further understood that a force may be applied by a machine or by automated equipment.

Base 30 has a socket, or channel or aperture, 40 for operatively connecting to engaging extension 51 of head 52. Socket 40 is adapted to removably accept an engaging extension 51 extending from head 52. Socket 40 is dimensioned and configured to slideably engage, or allow insertion to an operative depth of, engaging extension 51. Thus, base 30 may be removable from and/or transmit torque to or from engaging extension 51. The operative depth may be a depth of insertion of engaging extension 51 into socket 40 to allow the transfer of torque from engaging extension 51 to socket 40, or vice versa. It is understood that one or more engaging extensions 51 may engage one or more sockets 40.

Figure 3:
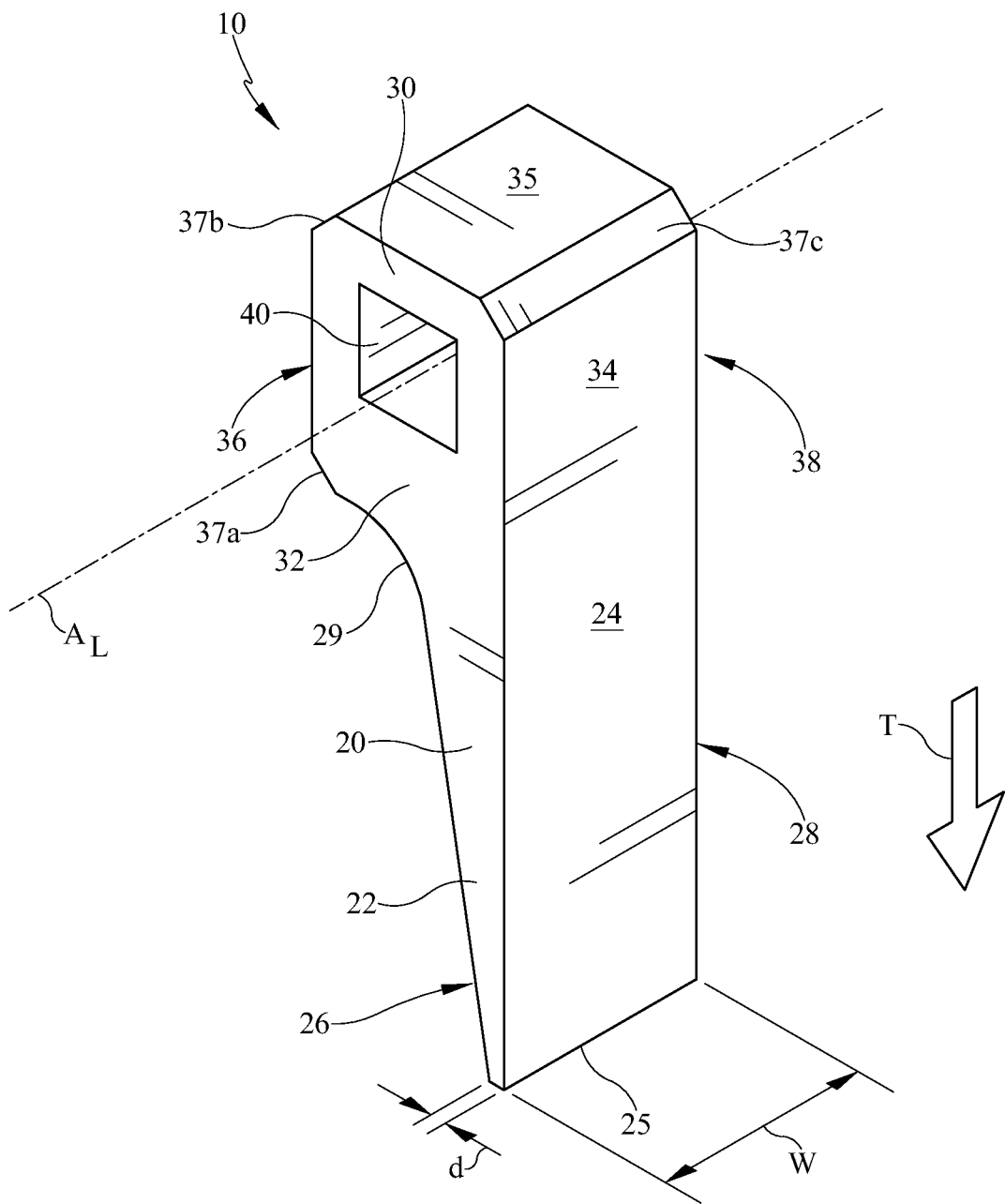
FIG. 3 is a perspective view of an embodiment of a chain link tester.
Figure 4:
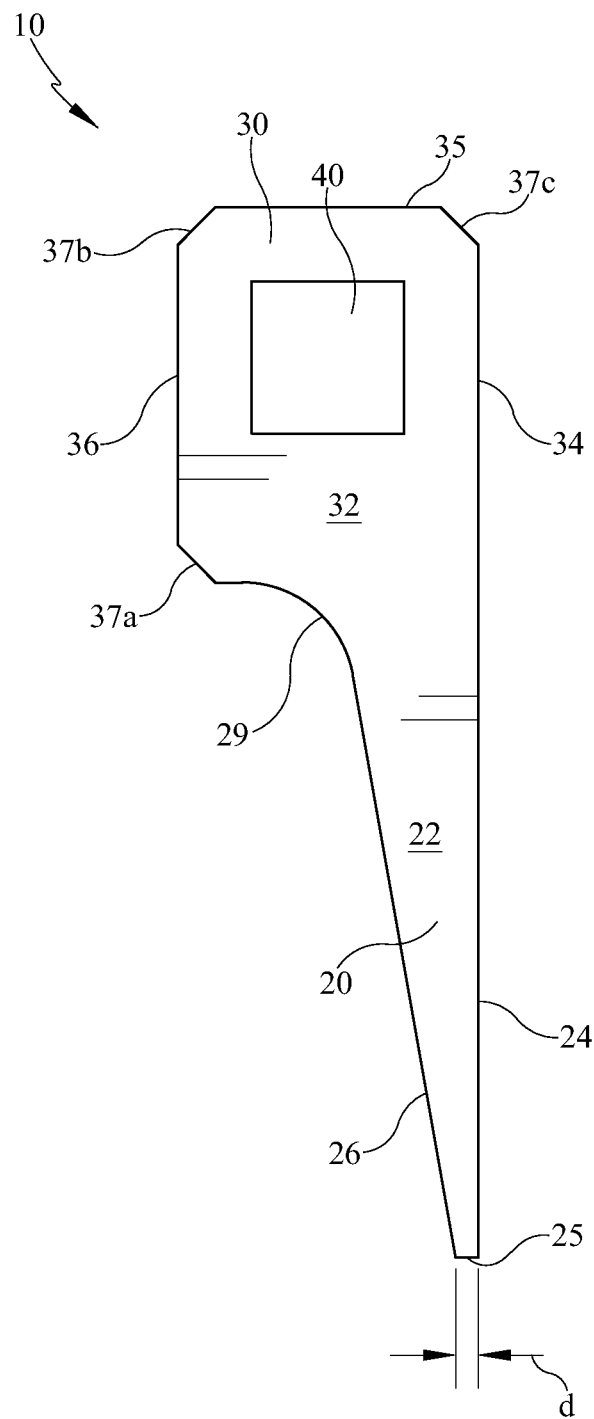
FIG. 4 is a first side view of an embodiment of a chain link tester.
Figure 5:
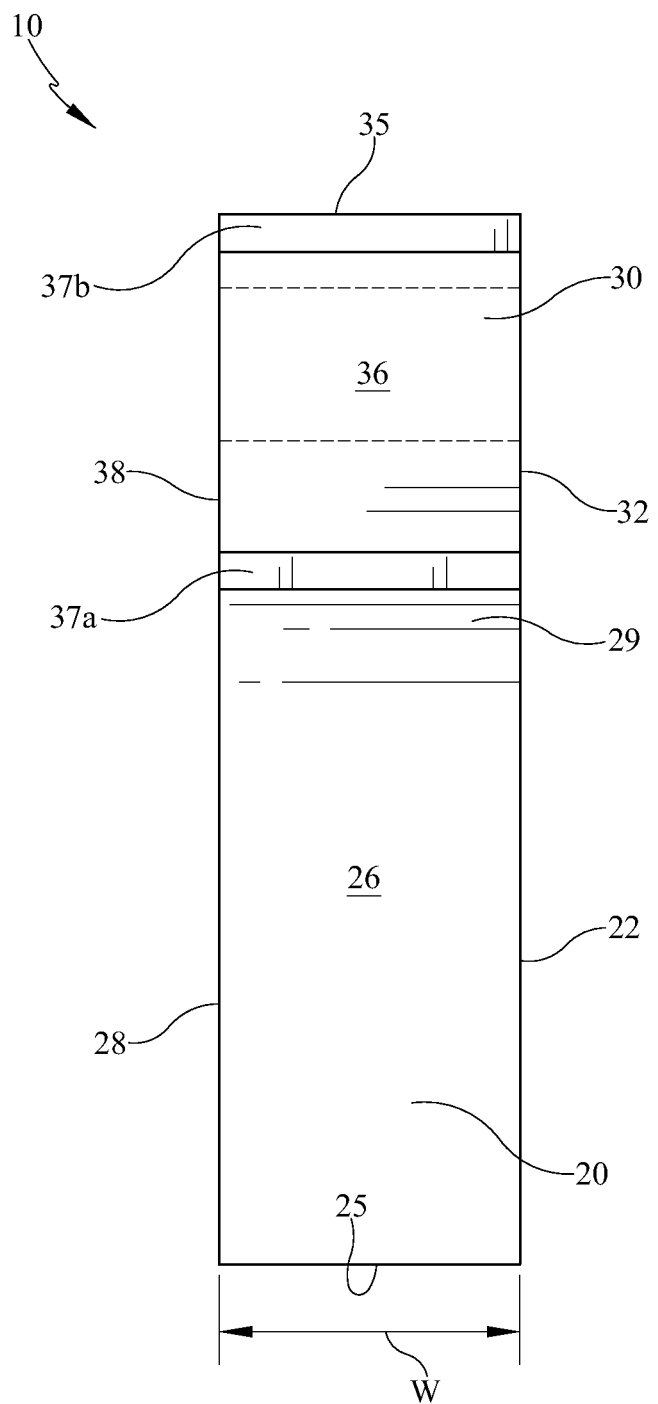
FIG. 5 is a second side view of an embodiment of a chain link tester.

Referring now to FIGS. 3-5, chain link tester 10 is illustrated having tapered lever 20, base 30, and socket 40. Socket 40 has a longitudinal axis $A_L$ and is sized and configured to connect to engaging extension 51 of torque wrench 50. Base 30 has a first side 32, a base first surface 34, a second side 38, a third side 36, a fourth side 35, as well as first, second, and third chamfers 37a, 37b, 37c, any or all of which, along with a corner radius 29 and/or tapered lever 20, may be included to substantially define the outer periphery of base 30. Socket 40 extends along longitudinal axis $A_L$ through first side 32 and second side 38, wherein longitudinal axis $A_L$ is substantially parallel to first surface 34. It is understood that socket 40 need not extend through both first side 32 and second side 38, and in some embodiments may only extend through either first side 32 or second side 38. However, it may be desirable that socket 40 extend through base 30 so that it may be connected to torque wrench 50 in more than one orientation. For example, in this embodiment, base 30 may be connected to torque wrench 50 with either first side 32 or second side 38 near, or adjacent to, torque wrench 50, thereby effectively allowing more orientations for operative connection to torque wrench 50. It is understood that handle 53 and a taper direction T need not be substantially parallel, as shown, and may be transverse or perpendicular to one another.

Socket 40 has a substantially square cross-section to correspondingly accept, or mate with, engaging extension 51 that similarly has a substantially square cross-section. It is understood that socket 40 may be any of a variety of shapes, sizes, and/or configurations, although it may be desirable to correspond with engaging extension 51 and/or to have at least one non-circular side to prevent rotation of engaging extension 51 within socket 40. For example, socket 40 and engaging extension 51 may have a cross-section or shape that is square, rectangular, triangular, hexagonal, octagonal, otherwise polygonal, trapezoidal, ovular, or any other shape. In some embodiments, chain link tester 10 may have, instead of or in addition to socket 40, an extension member that extends outwardly from base 30 along or parallel to longitudinal axis $A_L$, wherein the extension member may be adapted to connect to, for example, a socket of a torque metering device, or a dual socket that accepts it and an extension from a torque metering device such as engaging extension 51, or otherwise operatively connected to a torque metering device.

Chamfers 37a, 37b, 37c may be located at interfaces of corner radius 29 and third side 36, of third side 36 and fourth side 35, and of fourth side 35 and first surface 34, respectively. Chamfers 37a, 37b, 37c are not required in some embodiments, but may be desirable for, among other things, eliminating sharp edges and discomfort or injury from handling chain link tester 10, or for aiding in production of chain link tester 10, or for any other reason. It is understood that corner radius 29 need not extend to chamfer 37a, and one or more interposing sides, surfaces, or other features may be disposed between chamfers 37a, 37b, 37c and sides 35, 36, first surface 34, and/or corner radius 29. While base 30 is illustrated in the Figures as substantially box-like, it is understood that base 30 need not be box-like and, in some embodiments, may take any of a variety of forms and/or shapes, including, but not limited to, prismatic, cylindrical, round, spherical, bulbous, obloid, and/or any combination thereof. For example, in a bulbous or spherical form, base 30 may have only one substantially continuous outer surface, through which socket 40 may extend in one or more locations. Further, each of sides 32, 38, 36, 35 and first surface 34 may have a shape or form that is the same as, similar to, or distinct from, the others.

In some embodiments, tapered lever 20 may be coupled to base 30. Tapered lever 20 may be formed as one integral unit also including base 30, as illustrated, but, in some embodiments, tapered lever 20 may be otherwise connected or coupled to base 30. Corner radius 29 may be included in some embodiments for a variety of reasons, including, but not limited to, reducing stress concentrations at the interface of tapered lever 20 and base 30. Tapered lever 20 may include a tapered level first surface 24, a second surface 26, a first side 22, and a second side 28. Tapered lever 20 may further include a narrowing taper from base 30 to lever end 25 in taper direction T, formed by the angled relationship of first surface 24 and second surface 26. Tapered lever 20 may have a width W measured from first side 22 to second side 28 and perpendicular to taper direction T. Tapered lever 20 may also have a depth d measured from first surface 24 to second surface 26 and perpendicular to taper direction T and/or width W. Width W and/or depth d may be sized and configured to be inserted and engage one or more chain links 65 and/or sprocket 70 while chain link 65 is engaging sprocket 70 as, for example, chain link 65 may engage sprocket 70 during operation of a chain-and-sprocket drive. The narrowing taper may allow tapered lever 20 to be easily inserted between chain 60 and sprocket 70 (see FIGS. 1 and 2). Sprocket 70 may be attached to, connected to, and/or driven by being coupled or connected to a driver, such as, for example, a drive shaft or axle, at or near sprocket hub 75. The taper formed by tapered lever 20 may desirably be designed and/or made to optimize insertion and force application to a specific or pre-determined chain 60, sprocket 70, or the combination thereof. In this way, performance of chain link tester 10 may be optimized for a specific chain and/or sprocket that is being used in an application, such as, for example, an industrial dryer or other application.

Although it is not necessary that first surface 24 be planar as shown, it may be desirable in some embodiments that first surface 24 be planar to optimize the ease of insertion, the ability to meet relatively tight tolerances of chain 60 and/or sprocket 70, and/or the application of torque to the chain links 65 (see FIG. 2). First side 22 and second side 28 may be formed or dimensioned so that width W is smaller than a distance between sprocket teeth 72 and/or the length of chain link 65 to allow insertion of tapered lever 20 between a chain link 65 and sprocket 70. Further, width W and/or depth d may correspond to a certain or specified chain 60, chain link 65, sprocket 70 and/or sprocket tooth 72. In some embodiments, first side 22 and second side 28 may be angled relative to each other to form a narrowing taper in addition to or in lieu of the narrowing taper formed by first and second surfaces 24, 26. Lever end 25 is shown as substantially flat, but also may be pointed, rounded, or any of a variety of shapes or combinations thereof. In some embodiments, either or both of first and second surfaces 24, 26 may be angled, bent, or hooked, instead of substantially straight as shown. First surface 24 of tapered lever 20 and first surface 34 of base 30 are illustrated as co-planar, but it is understood that they do not need to be co-planar.

In use, chain link tester 10 may be provided and operatively connected to torque wrench 50 to allow transfer, or transmission, of torque to chain link tester 10 from a force applied in force direction F to torque wrench 50. Torque wrench 50 may be set to indicate when a desired, or pre-determined, amount of torque is applied thereto or to prevent or resist the transmission of more than the pre-determined amount of torque. The pre-determined amount of torque may be set by, for example, dial 55 or any other of a variety of adjusting, adjustable, or setting mechanisms. Chain link tester 10 may be caused to connect to torque wrench 50 by an operator or other individual or machine, or chain link tester 10 may be pre-connected to torque wrench 50. Chain link tester 10 may be inserted between chain 60 and sprocket 70, and/or between chain links 65 and sprocket teeth 72 by, for example, inserting lever end 25 until creating a wedge with either first surface 24 or second surface 26 contacting either chain 60 or sprocket 70, and the other of first surface 24 and second surface 26 contacting the other of chain 60 and sprocket 70. A force may be applied to torque wrench 50, for example at handle 54, in a force direction F to create a torque, or moment, about an axis parallel to or collinear with longitudinal axis $A_L$. The force applied to torque wrench 50 and/or a resulting torque may be transferred via said torque wrench 50 to chain link tester 10. The torque applied to chain link tester 10 may be metered, or measured, by torque wrench 50 to determine when an ascertainable or pre-determined amount of torque is being applied to chain link tester 10. Torque wrench 50 may indicate when the ascertainable or pre-determined amount of torque is applied to chain link tester 10 in any of a variety of ways, including, but not limited to audibly, visually, sensibly, or otherwise, such as, for example, as described herein. It is understood that one or more chain links 65 may be tested at once, and that one chain link tester 10 may be made to test more than one chain link 65 at a time. Further, any or all of these steps may be repeated or repeatable to, for example, test an entire length of chain 60. It should also be understood that particular or partial steps may be automated.

I claim:

1. A method for testing individual chain links in a chain, comprising:
    providing a chain link tester operatively connected to a torque metering device;
    inserting a lever of said chain link tester between a chain link and a sprocket, said chain link engaging said sprocket;
    using said torque metering device to apply a torque to said chain link tester; and
    using said torque metering device to determine when a pre-determined amount of torque has been applied to said chain link tester.

2. The method of claim 1 further comprising the step of providing an indication when said pre-determined amount of torque is applied to said chain link.

3. The method of claim 1 further comprising the step of adjusting a setting mechanism on said torque metering device to vary said pre-determined amount of torque.

4. An apparatus for testing individual chain links in a chain, comprising:
    a chain link tester having a base and a tapered lever that is insertable between an individual chain link and a sprocket while said individual chain link is engaging said sprocket;
    said tapered lever having a pair of opposed surfaces extending outwardly from said base,
        wherein the tapered level substantially defines the outer periphery of the base;
    said base rigidly coupled to said tapered lever, said base having a channel; and
    a torque metering device operatively connected to said chain link tester.

5. The apparatus of claim 4 wherein said torque metering device includes an indication when a pre-determined amount of torque has been applied to said torque metering device.

6. The apparatus of claim 5 wherein said indication is a meter.

7. The apparatus of claim 4 wherein at least one of said opposed surfaces is substantially planar.

8. The apparatus of claim 7 wherein said channel has a longitudinal axis parallel to said at least one planar surface.

9. The apparatus of claim 8 wherein said channel extends through an adapter.

10. An apparatus for testing individual chain links in a chain, comprising:
    a chain link tester having a base and a tapered lever that is insertable between an individual chain link and a sprocket while said individual chain link is engaging said sprocket;
    said tapered lever having a pair of opposed surfaces extending outwardly from said base,
        wherein the tapered level substantially defines the outer periphery of the base;
    a base rigidly coupled to said tapered lever; and
    an extension member extending outwardly from said chain link tester and adapted to operatively connect to a torque metering device.

11. The apparatus of claim 10 wherein said torque metering device includes an indication when a pre-determined amount of torque has been applied to said torque metering device.

12. The apparatus of claim 11 wherein said indication is a meter.

13. The apparatus of claim 10 wherein at least one of said opposed surfaces is substantially planar.

14. The apparatus of claim 13 wherein said extension member extends in a longitudinal direction parallel to said at least one planar surface.

15. A chain link testing apparatus, comprising:
   a tapered lever having a narrowing taper in a taper direction;
      said tapered lever having a width dimension perpendicular to said taper direction, said width dimension sized and configured to fit between chain links;
      said tapered level having a depth dimension perpendicular to said taper direction or said width dimension, wherein said depth dimension is smaller than a base and configured to fit between chain links;
   a base rigidly coupled to said tapered lever and having at least one surface and an
      aperture suitable for removably attaching said base to a torque metering device;
      said aperture extending in a longitudinal direction through said at least one surface;
      said longitudinal direction substantially perpendicular to said taper direction; and
      said narrowing taper of said tapered lever narrowing away from said base.

16. The chain link testing apparatus of claim 15 wherein said base is operatively connected to said torque metering device.

* * * * *